United States Patent
Müller et al.

(10) Patent No.: US 7,186,988 B2
(45) Date of Patent: Mar. 6, 2007

(54) METHOD FOR ANALYZING CHEMICAL AND OR BIOLOGICAL SAMPLES

(75) Inventors: Jürgen Müller, Hamburg (DE); Stefan Hummel, Haseldorf (DE)

(73) Assignee: Evotec OAI AG, Hamburg (DE)

( * ) Notice: Subject to any disclaimer, the term of this patent is extended or adjusted under 35 U.S.C. 154(b) by 236 days.

(21) Appl. No.: 10/471,042

(22) PCT Filed: Mar. 5, 2002

(86) PCT No.: PCT/EP02/02372

§ 371 (c)(1),
(2), (4) Date: Jul. 7, 2004

(87) PCT Pub. No.: WO02/071043

PCT Pub. Date: Sep. 12, 2002

(65) Prior Publication Data

US 2004/0238729 A1    Dec. 2, 2004

(30) Foreign Application Priority Data

Mar. 6, 2001    (DE) ................................ 101 10 594

(51) Int. Cl.
*H01J 3/14* (2006.01)

(52) U.S. Cl. .................................. 250/458.1; 250/234

(58) Field of Classification Search ................ 250/234, 250/235, 236, 233, 230, 225, 216, 458.1; 356/328

See application file for complete search history.

(56) References Cited

U.S. PATENT DOCUMENTS

| 6,236,457 B1 * | 5/2001 | Allen et al. ............. 356/328 |
| 6,310,687 B1 * | 10/2001 | Stumbo et al. ........... 356/317 |
| 6,377,346 B1 * | 4/2002 | Vaisala et al. ........... 356/417 |
| 6,813,050 B2 * | 11/2004 | Chen et al. .............. 359/201 |
| 6,965,105 B2 * | 11/2005 | Oldham et al. ........... 250/236 |

FOREIGN PATENT DOCUMENTS

| DE | G 89 04 152.6 | 9/1989 |
| DE | 692 27 902 T2 | 11/1992 |
| DE | 19950225 A1 | 5/2000 |
| JP | 03248793 A | 11/1991 |
| WO | WO02/06796 A2 | 1/2002 |

OTHER PUBLICATIONS

German Examination Report, dated Jun. 22, 2001.

* cited by examiner

*Primary Examiner*—Otilia Gabor
*Assistant Examiner*—Faye Boosalis
(74) *Attorney, Agent, or Firm*—Griffin & Szipl, P.C.

(57) ABSTRACT

In a method for analyzing a chemical and/or biological sample, particularly in high- and medium throughput screening systems, an observation beam (12) is focused in an observation volume (24) of the sample. For analyzing the sample, the observation beam (12) is moved in the sample. According to the inventions, to improve the quality of the measurement, the observation beam is moved continuously in the observation volume (24).

16 Claims, 2 Drawing Sheets

METHOD FOR ANALYZING CHEMICAL AND OR BIOLOGICAL SAMPLES

Figure 1:
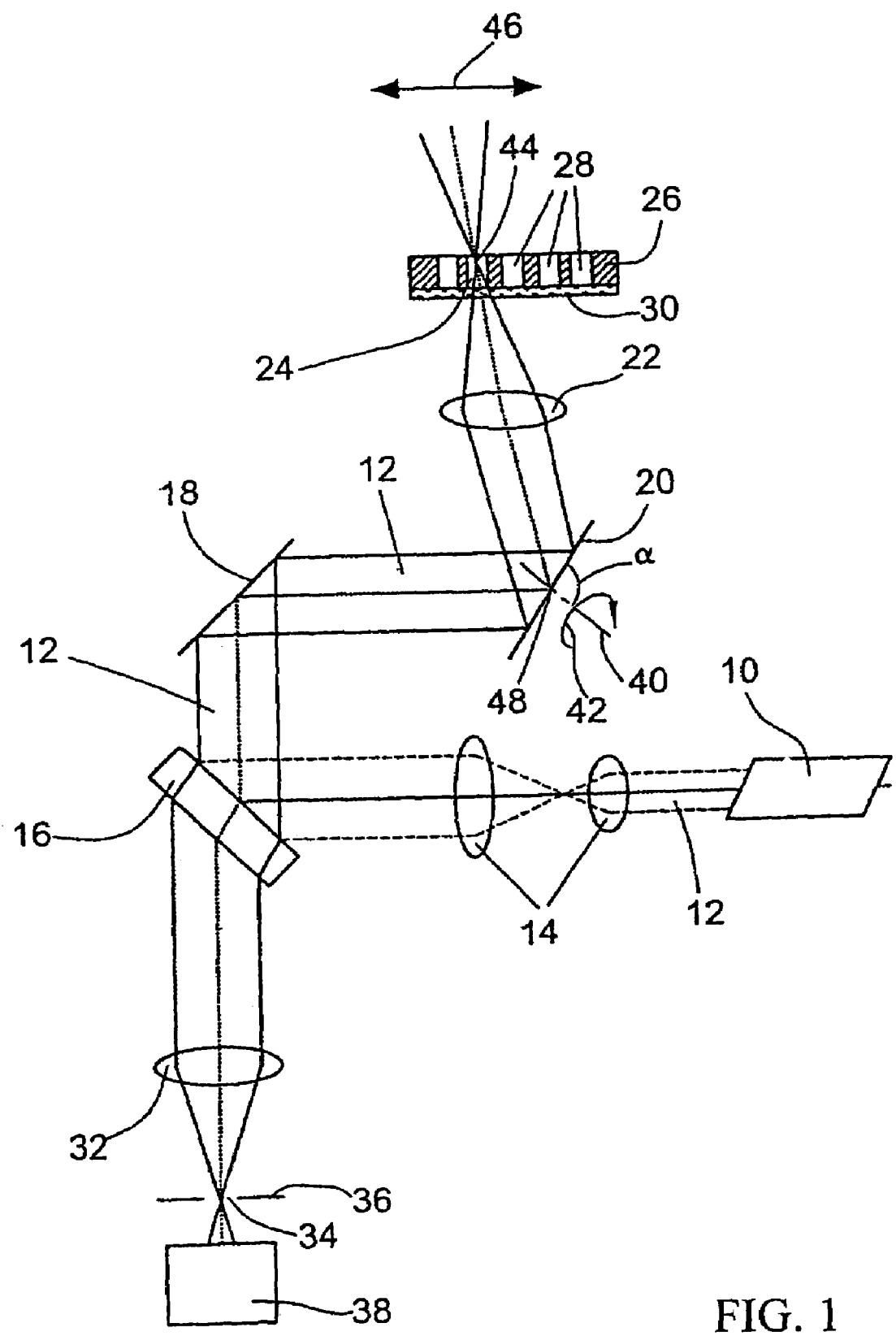

The invention relates to a method for analyzing chemical and/or biological samples, particularly in high- and medium throughput screening. Further, the invention relates to a microscope for performing said method, as used particularly in fluorescence spectroscopy.

Microscopes serve for the optical coverage of the processes taking place in an observation volume. Known confocal microscopes comprise an illumination unit, e.g. a laser, for generating an observation beam, particularly in the form of exciting light. The exciting light, optionally after conditioning by a lens arrangement, is incident onto a dichroic mirror which will reflect the light in the direction of the observation volume. Thereafter, the light is directed to pass through a lens system, particularly a microscope objective, which will focus the light in the observation volume. In the observation volume, which includes e.g. biological and/or chemical samples, e.g. fluorescence is generated by the exciting light depending on the respective composition of the samples. The thus generated fluorescent light passes (through the microscope objective and through the dichroic mirror to a detector unit. An aperture stop can be provided before the detector unit, with the fluorescent light focused into the aperture stop; thus, a confocal microscope is obtained.

In confocal microscopes, which have generally proven useful in practical use, a problem exists in that the molecules—particularly in case of large molecules—will move only slowly due to the Brownian molecule movement. Therefore, it may happen that the molecule under observation will pass through the focus of the microscope objective only after an extended period of time. This can have the effect that the results of the measurements are impaired, e.g. because the reactivity or the fluorescence emission of the molecule has already decreased again. Further, particularly in high- and medium throughput screening, i.e. when examining a large number of samples at brief time intervals, it is disadvantageous if a sample has to be observed for a relatively long period of time before a result can be obtained.

To fulfill the resultant demands, it is possible e.g. to move the sample. This involves a comparatively complex process and may cause undesired movements or reactions within the sample. This in turn can again impair the measurement results.

As a further possibility, it can be provided to move the beam of the exciting light. A known approach for moving the light beam resides in the provision of one or a plurality of mirrors in the beam path of the microscope, which mirrors can be tilted back and forth by means of a drive mechanism. The provision of two mirrors offers the possibility to move the light beam within a plane of the observation volume. Arrangements of this type have the disadvantage that the tilting movement of the mirror has a dead center so that the movement of the light beam will be decelerated and accelerated. This causes a non-uniform excitation of the universe within the sample and will thus impair the measurement results. The primary reason lies in the fact that, at the dead center, the fluorescence molecule is irradiated longer and can thus emit more photons or that the molecule is bleached more intensely. Further, microscopes with tiltable mirrors entail the disadvantage that the light beam passes through the objective at different angles relative to the optical axis of the microscope objective. This causes an optical error which varies in dependence of the inclination of the tilt angle and likewise has a negative influence on the measurement results. Further, the focus of a light beam directed obliquely through the microscope objective will assume an oval shape. Thus, also the shape of the focus will change in dependence of the orientation of the tilting mirror. Thereby, too, the measurement results are adversely affected.

The above outlined disadvantages exist in conformal microscopes and other microscopes alike. Especially in high- and medium throughput screening, the measurement data must be taken in a very short time. This has the consequence that fluorescence markers have to be excited with relatively high energy. In this situation, already slight irregularities in excitation, particularly a too long excitation of the markers, lead to an impairment of the measurement results and possibly to destruction of the markers.

It is an object of the invention to provide a method for analyzing chemical and/or biological samples, particularly for high- and medium throughput screening, which makes it possible to move the focus through the observation volume while obtaining improved measurement results. Further, it is an object of the invention to provide an apparatus for performing said method.

According to the invention, the above object is achieved by the features of claims 1 and 8, respectively.

In the inventive method, the movement of the observation beam is performed substantially continuously. The movement of the observation beam or the exciting light in the observation volume of the sample is thus carried out without a reversal of directions which would lead to a considerable deceleration and acceleration of the movement of the light beam. Notably, when examining samples which are to be excited to generate fluorescence, the above uniformization of the movement of the light beam in the observation volume will make the excitation highly uniform. In this manner, for instance, destruction of fluorescence markers by increased excitation is prevented. By the uniformity of the movement of the observation beam through the observation volume, the quality of the measurement results can be considerably improved.

A further advantage of the inventive method resides in that a constant or uniform movement of the observation beam through the sample allows for a better realization of the fluctuation times of individual particles such as e.g. molecules (FIMDA measurements). This is made possible since, when determining the fluctuation times, consideration has to be given to the moving speed of the observation beam. In this regard, a constant or nearly constant speed of the observation beam is much more easily considered. Further, the observation times per particle are rendered uniform. This means e.g. that of each particle the same number of information items is detected. Thereby, the statistic quality of the data is considerably improved.

According to the invention, the observation beam can be a beam generated by an illuminating device such as e.g. a laser; by the inventive method, this beam is caused to carry out a uniform movement in the sample. The observation beam in this case will comprise e.g. exciting light. Further, the observation beam can also be the beam path of the observation. The beam path in this case extends in reverse direction. In this case, the region observed by the detector is moved in the sample. Thus, what is observed is e.g. the fluorescence of a sample, i.e. the radiation emitted from the sample.

Preferably, the movement of the observation beam is unidirectional. A reversal of the direction of movement is thus avoided. As a consequence, massive variations within the illumination volume of the generated or observed quantity of photons, i.e. variations on different illumination or observation sites, are avoided. The quantity of photons in the present context is defined as the number of the generated or emitted photons per site. Thus, the quantity of photons is the intensity integrated over time. In case of a constant speed of movement of the observation beam in the sample, the dwell period of the beam at each site of the sample is constant or undergoes deviations within considerably tighter limits than in known methods. Thereby, the quality of the measurement results can be considerably improved. Preferably, the illumination beam is moved along a path closed in itself, preferably along an elliptic path, and still more preferably along a substantially circular path.

In performing the movement of the observation beam in the observation volume, it is particularly preferred to use a deflection mirror which is rotatable about an axis of rotation. In this regard, the axis of rotation includes an angle ≠90° together with the area of the deflection mirror. By the thus generated tumbler movement of the deflection mirror, the observation beam is moved along an elliptic path in the observation volume. In this manner, when compared to a reciprocating movement of the observation beam, differences of the dwell periods at individual illumination sites within the observation volume are significantly reduced.

However, due to the elliptic shape of the path, the moving speed of the observation beam in the observation volume is not constant. Particularly in the region of the apex of the ellipse, the observation beam has a lower speed. Therefore, according to the invention, it is particularly preferred to make the dwell period of the observation beam uniform by varying the rotational speed of the deflection mirror. This means that the rotational speed is set in such a manner that the observation beam in the observation volume has a speed which is deviating at the most within narrow limits. Preferably, the speed is substantially constant.

In a further preferred embodiment, the uniformization of the illumination intensity acting on different illumination sites in the sample and varying particularly in dependence of the dwell period, i.e. of the moving speed of the observation beam or the exciting beam, is effected by controlling the intensity of the observation beam in dependence of the moving speed. The photon quantity generated by the observation beam is made uniform by speed-dependent control of the illumination intensity. According to the invention, the intensity of the observation beam will thus be reduced when the observation beam is moving at a relatively slow speed in the observation volume. Also thereby, a uniformization of the measurement results can be effected. Especially in case of measurements based on fluorescence, it can thus be accomplished that the individual particles are excited in a uniform manner. Thus, an impairment of the measurement results due to non-uniform excitation or a destruction of the fluorescence markers are avoided.

The control of the intensity of the observation beam which can be performed e.g. by time-dependent modulation of a laser, is an invention in its own right which is independent from the continuous movement of the observation beam. For instance, also in case of a simple reciprocating movement of the observation beam, e.g. by a tilting mirror, a uniformization of the illumination intensity can be obtained by corresponding control of the intensity of the illumination beam. Particularly preferred, however, is a uniformization through a combination of the speed variation and the varying of the illumination intensity. This offers the advantage that the speed of the e.g. rotating deflection mirror need by varied only slightly so that the occurring moments of inertia do not become too high. Also the varying of the intensity of the illumination beam can be realized in a considerably simpler manner in case of small adjustments than in case of large deviations.

The adapting of the illumination intensity can also be performed e.g. by filters to be adapted to the shape of the path.

For performing the inventive method, the microscope comprises a deflection mirror arranged to deflect an observation beam, e.g. excitation light, generated by an illumination unit. Thereby, the focus is moved in the observation volume. Instead of a tilting movement, the deflection mirror performs a tumble movement. By the tumble movement, the focus is moved along a closed path in the observation volume. The movement will thus be continuous. A complete braking and subsequent acceleration of the light beam as occurring in tiltable mirrors will thus not take place in a mirror arranged for tumble movements. Further, the inventive configuration of the microscope can be realized at considerably lower cost than the provision of tiltable mirrors or so-called galvo scanners which require complex drive and control electronics. Further, since the inventive apparatus is adapted to realize a continuous movement of the light beam on a path and to avoid strong braking and accelerating movements, higher scanning speeds are possible as compared to those obtained when using tiltable mirrors. When use is made of tiltable mirrors, particular consideration has to be given to the large mass moment of inertia of the mirrors which prevents fast movements of the mirror. Further, fast movements of the mirrors may give rise to vibrations which will impair the measurements.

Further, the inventive microscope can be used to perform the above method merely for observation of the sample. In such a microscope, it is not provided that a beam generated by an illumination unit is caused to perform a tumble movement. In this case, the tumble mirror or another suitable device is employed to cause the site observed by an observation detector to be moved in the sample.

The tumble movement can be performed e.g. by a three-point suspension at the rear of the mirror. Thus, by moving the individual suspension points, the mirror can be caused to perform tumble movements.

According to a preferred embodiment, the mirror is rotated about an axis of rotation. In this case, the deflection mirror and the axis of rotation include an angle unequal to 90°. Alone by the rotation of the mirror, a tumble movement and thus a corresponding movement of the light beam in the observation volume will be generated.

In a microscope for the examination of minimum samples which can be e.g. in the microliter or sub-microliter range, the angle of the deflection mirror relative to the axis of rotation is in the range of 90.1°–95°, preferably 90.1°–92°, still more preferably 90.1°–91°. Assuming a typical focal length f=5 of the objective, this will lead to circular movements with radii r=f·tan (d−90°)=8 μm–450 μm (preferably 8 μm–180 μm, most preferably 8 μm–90 μm).

In a mirror performing a tumble movement, a circular movement is effected preferably in that the beam path is arranged in parallel to the axis of rotation. Using a beam extending at an angle to the axis of rotation, the observation beam will perform an elliptic movement in the sample or the observation volume.

Preferably, the observation beam is moved in such a manner that the focus in the observation volume will be moved along a closed path. In this regard, one has to consider the tumble movement in dependence of the surface of the mirror and the reflection point of the light beam on the mirror relative to the center of the tumble movement. In case of a tumble movement generated by rotation and a preferably plane deflection mirror, good measurement results can be obtained by having the excitation light impinge on the deflection mirror substantially in the rotational center of the mirror. Such an arrangement has the advantage that the light beam will pass the measurement objective always at the same distance to the central axis of the measurement objective. Therefore, the deterioration of the focus relative to a light beam passing the objective in the axis of the objective is substantially constant and thus can be compensated for in a well-aimed manner by corresponding adjustment. Thus, since no change of the focus in dependence of the position of the mirror or the position of the focus in the sample is brought about, considerably improved measurement results can be obtained.

Preferably, the angle of the mirror is adjustable relative to the axis of rotation or relative to a light beam incident on the deflection mirror. For this purpose, there can be provided e.g. an adjustment unit for automatic adjustment of the angle of the deflection mirror. This has the advantage that e.g. also during the examination of a sample the angle of the deflection mirror and thus the path of the focus in the sample can be varied. In case of an exciting beam incident in the rotational center of the deflection mirror, the radius of the circular movement of the focus or the main axes of the ellipse in the sample can be changed by adjusting the above angle. In this manner, a complete scanning of the sample in a plane can be realized.

A further possibility for a complete scanning of the sample in a plane resides in that the angle of the deflection mirror is kept constant during the examination so that the focus will move on an unchanged path. For scanning the sample, the platform holding the sample under examination will now be moved as well. The movement of the platform can be one- or two-dimensional. Further, if the confocal principle is used, it is possible to combine the two above methods for scanning a sample particularly in a plane.

Further, in a microscope, the existing dichroic mirror serving as beam splitter can be configured for use as a deflection mirror which is adapted to perform a suitable tumble movement. For this purpose, the dichroic mirror is preferably supported in a connecting link guide. The rotation is imparted from outside so that the beam path will not be affected. Since such a movement of the beam splitter will also result in a corresponding movement of the picture imaged on the detector, the detector used in this embodiment is preferably an area sensor, e.g. a large-surfaced photodiode. In case of a non-confocal microscope, the detector area can be read in an integrated manner by means of a large-surfaced photodetector because the light incident on the detector will generate the same signal irrespective of the side where it impinges on the detector.

Preferably, the above described microscope is a confocal microscope. In a confocal microscope, the measurement results can be considerably improved by use of the inventive deflection mirror.

A further embodiment of the invention relates to a deflection unit for a microscope for optical coverage of an observation volume. The deflection unit comprises a deflection mirror connected to a drive unit and adapted to perform a tumble movement through the drive unit. The deflection unit is an additional component which can be connected to a conventional microscope.

For this purpose, the deflection unit comprises a casing supporting the drive unit and/or the deflection mirror. The casing comprises a connection element for connection to an objective receiving portion of a microscope, and a receiving element for receiving a microscope objective. Thus, for instance, it is possible to remove the microscope objective from a conventional microscope, to insert the deflection unit into the objective receiving portion instead, and to attach the previously removed microscope objective to the receiving element on the casing. Thus, a conventional microscope can be conveniently retrofitted with the deflection unit to obtain the inventive microscope with tumbling mirror.

The deflection mirror provided in the inventive deflection unit can comprise the above described modifications.

The above described deflection unit is particularly suited for use in a confocal microscope.

Preferred embodiments of the invention will be described in greater detail hereunder with reference to the accompanying drawings.

Figure 2:
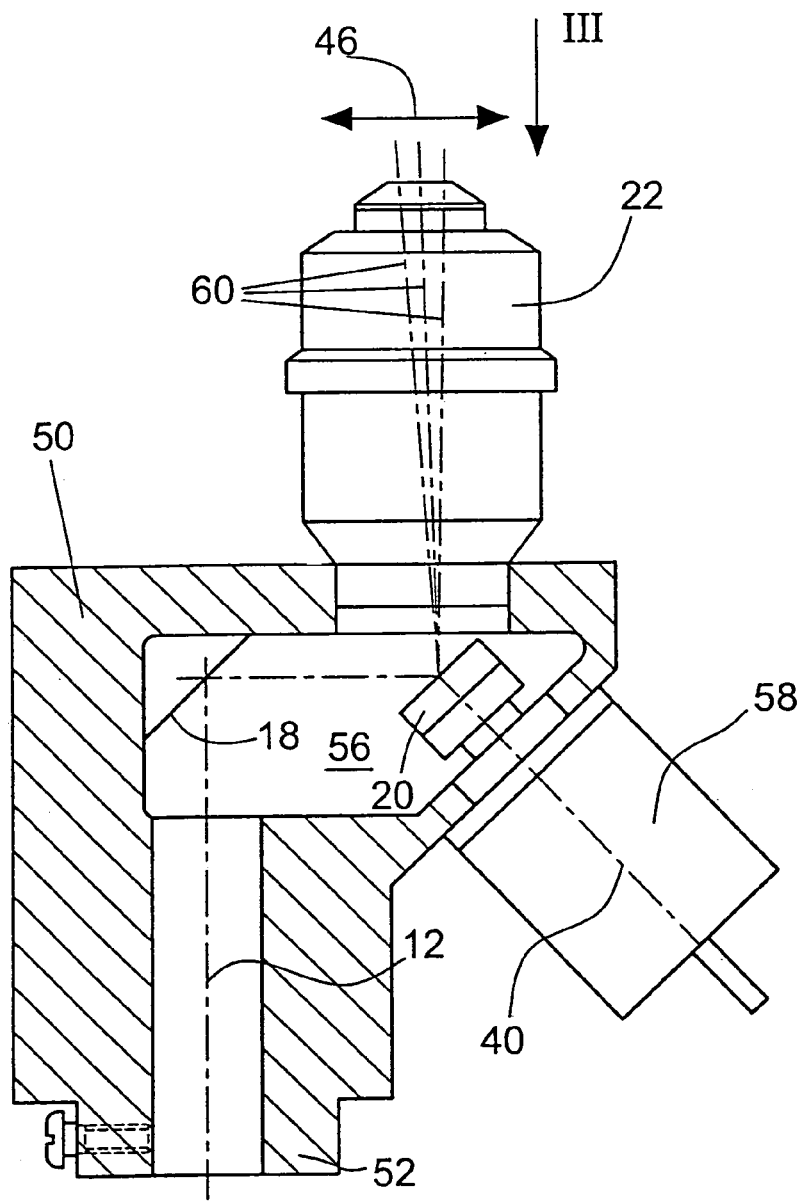
Figure 3:
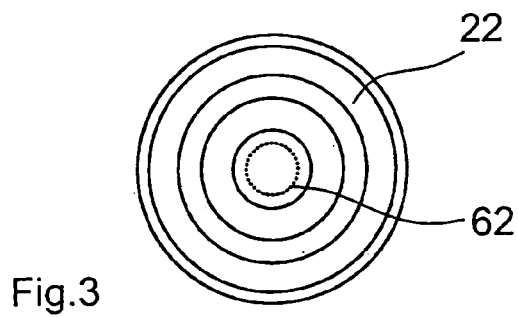

In the drawings:

FIG. 1 is a schematic view of a confocal microscope comprising a deflection mirror to be rotated as provided by the invention, FIG. 2 is a partially sectional schematic side view of a deflection unit according to the invention, and FIG. 3 is a plan view in the direction of the arrow III in FIG. 2, of the microscope objective shown in FIG. 2.

The confocal microscope schematically illustrated in FIG. 1 comprises an illumination device 10 provided as a laser. The excitation light 12 generated by the laser is directed to a beam splitter 16 by means of a lens arrangement 14. Beam splitter 16 guides the excitation light towards a reflection mirror 18. The latter reflects the excitation light back towards a deflection mirror 20 which will reflect the excitation light towards a microscope objective 22. Microscope objective 22 is arranged to focus the excitation light 12 back into an observation volume 24.

In the illustrated embodiment, the observation volume 24 is provided as a deepened portion of a titration plate 26 whose openings 28 are closed by a glass bottom 30.

The light emitted by the sample arranged in the deepened portion 28 is guided in the reverse direction through the microscope objective and is reflected by deflection mirror 20 and reflection mirror 18 towards beam splitter 16. By means of the beam splitter 16, the light coming from the observation volume 24 is deflected towards a tube lens 32. Tube lens 32 will focus the light in an opening 34 of an aperture stop 36. Thereafter, the light is incident on a detector unit 38.

In the illustrated example, the reflection mirror 18 is arranged at an angle of 45° relative to the exciting light 12. In this manner, a deflection of the exciting light 12 from the usual beam path is effected. This has the advantage that a drive unit for the deflection mirror 20 can be simply arranged outside the beam path. Further, the customary configuration of the confocal microscope arranged to have a sample illuminated from below, is maintained.

Deflection mirror 20 performs a tumble movement by being rotatable about an axis of rotation 40 in the direction of an arrow 42. The mirror 20 together with the axis of rotation includes an angle α unequal to 90°. This angle α is the larger one of the two angles between the axis of rotation 40 and the mirror 20. By the rotation of mirror 20, the angle of incidence of the exciting light 12 coming from reflection mirror 18 will be changed depending on the rotational position of deflection mirror 20. Thereby, in the projection shown in FIG. 1, the focus 44 in observation volume 24 will move in the linear direction as indicated by arrow 46. When viewed from above, focus 44 moves on a closed path configured as an ellipse. If the exciting light impinges on the deflection mirror 20 substantially in the center of rotation 48, the circular movement is concentric with the beam axis.

The deflection unit illustrated in FIGS. 2 and 3 is provided as an add-on part for a conventional confocal microscope. The deflection unit has a casing 50. Casing 50 is provided with a connection element 52. This element can be e.g. a clamping means. Using a suitable adapter, the deflection unit can be connected to an objective receiving portion of the usual type. For connecting the connection element to the confocal microscope, the connection element is connected with the receiving portion normally serving for receiving the microscope objective 22. For this purpose, the microscope objective 22 is unscrewed from the corresponding support portion, and the deflection unit is screwed into the corresponding receiving portion of the confocal microscope by means of the connection element 52, and, if required, by use of an added adapter.

Internally of the casing, a reflection mirror 18 is provided at an angle of substantially 45° relative to the exciting light 12. In the illustrated example, reflection mirror 18 is a prism.

Further, the mirror 20 is arranged in a cavity 56 of casing 50. Mirror 20 is arranged at an angle to the axis of rotation 40 corresponding to mirror 20 illustrated in FIG. 1. For driving the deflection mirror 20 in a rotational movement, a drive unit 58 such as e.g. an electric motor is provided. By rotation of deflection mirror 20, the beam of the exciting light 12 is deflected as indicated by the interrupted lines 60 in the microscope objective 22. In the projection shown in FIG. 2, there is thus again performed a movement of the deflection light in the direction of arrow 46. When viewing the objective 22 from the top (FIG. 3), the exciting light is moved along an ellipse 62.

The invention claimed is:

1. A method for analyzing a chemical and/or biological sample, particularly in high and medium throughput screening systems, comprising the following steps: focusing an observation beam in an observation volume of the sample and continuously moving the observation beam in the observation volume of the sample by deflecting the observation beam by means of a deflection mirror which performs a tunable movement and together with an axis of rotation including an angle (a) in the range of 90.10° to 95°.

2. The method according to claim 1, characterized in that the observation beam is moved undirectionally.

3. The method according to claim 1 or 2, characterized in that the observation beam is moved along a path closed in itself.

4. The method according to claim 1 or 2, characterized in that, for uniformization of the dwell period of the observation beam at illumination sites in the observation volume, the rotational speed of the deflection mirror is varied.

5. The method according to claim 1 or 2, characterized in that, for uniformization of the photon quantity acting on illumination sites of the sample, the intensity of the observation beam is controlled in dependence of the moving speed of the observation beam in the observation volume.

6. The method according to claim 1 or 2, characterized in that, under the influence the observation beam, particles contained in the sample are excited to generate luminescence.

7. The method according to claim 6, characterized in that the radiation emitted by the particles, especially fluorescence radiation, is detected.

8. A microscope for performing the method according to claim 1 or 2, comprising an illumination unit for generating an exciting light, a microscopic objective for focusing the exciting light in the observation volume, and a deflection mirror arranged to deflect the exciting light to move the focus in the observation volume, the deflection mirror performing a tumble movement characterized in that an angle between the deflection mirror and an axis of rotation in the range of 90.10° to 95°.

9. The microscope according to claim 8, characterized in that the exciting light is incident on the deflection mirror substantially in the center of rotation of the deflection mirror.

10. The microscope according to claim 8, characterized in that the angle (a) of the deflection mirror is adjustable.

11. The microscope according to claim 10, characterized in that an adjustment unit is provided for automatic adjustment of the angle (a) of the deflection mirror.

12. The microscope according to claim 8, characterized in that the deflection mirror is planar.

13. A deflection unit for a microscope according to claim 8 for optical coverage of an observation volume, comprising a deflection mirror connected to a drive unit and adapted to perform a tumble movement imparted by the drive unit, the deflection mirror together with an axis of rotation including an angle (a) in the range of 90.10° to 95°.

14. The deflection unit according to claim 13, characterized by a casing supporting the drive unit and/or the deflection mirror, provided with a connection element for connection to an objective receiving portion of a confocal microscope, and with a receiving element arranged to receive a microscope objective.

15. The microscope according to claim 8, characterized by a reflection mirror arranged vertically to the axis of rotation of the deflection mirror.

16. A microscope for performing the method according to claims 1 or 2, characterized by a beam splitter by which the exciting light coming from the illumination unit is guided toward the observation volume, and which transmits the light emitted from the observation volume, the beam splitter further serving as a deflection mirror.

* * * * *